(12) United States Patent
Ono et al.

(10) Patent No.: US 12,394,047 B2
(45) Date of Patent: Aug. 19, 2025

(54) ANALYSIS ASSISTING DEVICE, ANALYSIS ASSISTING SYSTEM, AND RECORDING MEDIUM

(71) Applicant: CANON MEDICAL SYSTEMS CORPORATION, Tochigi (JP)

(72) Inventors: Ryoichi Ono, Utsunomiya (JP); Takahiko Nishioka, Otawara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 387 days.

(21) Appl. No.: 17/822,906

(22) Filed: Aug. 29, 2022

(65) Prior Publication Data

US 2023/0067053 A1 Mar. 2, 2023

(30) Foreign Application Priority Data

Aug. 30, 2021 (JP) ................. 2021-140155

(51) Int. Cl.
  *G16H 30/40* (2018.01)
  *G06T 7/00* (2017.01)

(52) U.S. Cl.
  CPC ........... *G06T 7/0012* (2013.01); *G16H 30/40* (2018.01)

(58) Field of Classification Search
  CPC .................................................. G06T 7/0012
  See application file for complete search history.

(56) References Cited

U.S. PATENT DOCUMENTS

2011/0054295 A1 3/2011 Masumoto et al.
2019/0364168 A1* 11/2019 Nishikai ................ G06F 3/121

2021/0121146 A1* 4/2021 Inomata .................... A61B 6/54
2021/0158105 A1* 5/2021 Machida ............ G06V 10/7784
2021/0304384 A1* 9/2021 Nakada ............. H04N 1/00087

FOREIGN PATENT DOCUMENTS

CN  106941579 B  *  3/2019  .............. H04N 1/04
JP  2007-282844 A  11/2007
JP  2011-92677 A  5/2011
(Continued)

OTHER PUBLICATIONS

Japanese Office Action issued Feb. 26, 2025 in Japanese Patent Application No. 2021-140155, 3 pages.

*Primary Examiner* — Di Xiao
(74) *Attorney, Agent, or Firm* — Oblon, McClelland, Maier & Neustadt, L.L.P.

(57) ABSTRACT

An analysis assisting device according to an embodiment includes processing circuitry. The processing circuitry is configured to obtain first analysis image data obtained on the basis of an image taken of a patient and additional information of the image; to obtain an analysis result of analyzing the first analysis image data; to output, when the analysis result does not satisfy a predetermined condition, an image processing condition optimal for the analysis; either to obtain second analysis image data by generating the second analysis image data by performing an image processing process on the basis of the image processing condition; or to obtain the second analysis image data generated as a result of an external device performing an image processing process on the basis of the image processing condition; and to obtain an analysis result of analyzing the second analysis image data.

13 Claims, 7 Drawing Sheets

(56) References Cited

FOREIGN PATENT DOCUMENTS

| | | |
|---|---|---|
| JP | 2012-90659 A | 5/2012 |
| JP | 2019-54896 A | 4/2019 |
| JP | 2021-509721 A | 4/2021 |
| JP | 7021321 B1 * | 2/2022 |
| WO | WO 2019/136349 A2 | 7/2019 |

* cited by examiner

FIG.3

RECEPTION IS COMPLETED;
EXECUTION IS UNDERWAY

FIG.4

ANALYSIS IS COMPLETED

ANALYSIS
RESULT

FIG.5

RECONSTRUCTION AND RE-ANALYSIS ARE UNDERWAY
(PROCESS FOR PERFORMING RE-PROCESSING IS UNDERWAY)
ANALYSIS USING INITIAL (FIRST) IMAGE PROCESSING
CONDITIONS FAILED.
IMAGE PROCESSING CONDITIONS FOR RE-PROCESSING:
AA, BB···

ANALYSIS ASSISTING DEVICE, ANALYSIS ASSISTING SYSTEM, AND RECORDING MEDIUM

CROSS-REFERENCE TO RELATED APPLICATIONS

This application is based upon and claims the benefit of priority from Japanese Patent Application No. 2021-140155, filed on Aug. 30, 2021; the entire contents of which are incorporated herein by reference.

FIELD

Embodiments described herein relate generally to an analysis assisting device, an analysis assisting system, and a recording medium.

BACKGROUND

A platform is known by which data in a Digital Imaging and Communications in Medicine (DICOM) scheme (hereinafter, "DICOM data") generated by a medical image generating device such as an X-ray Computed Tomography (CT) apparatus or a Magnetic Resonance Imaging (MRI) apparatus is received and the received DICOM data is automatically forwarded to an analysis application. The DICOM data includes reconstructed image data and various types of additional information (tags).

BRIEF DESCRIPTION OF THE DRAWINGS

FIG. 3 is a drawing illustrating an example of a message displayed while the processes at steps S101 through S110 are performed according to the first embodiment;

FIG. 4 is a drawing illustrating examples of a message and an analysis result output at step S111 according to the first embodiment;

FIG. 5 is a drawing illustrating an example of a message displayed while the processes at steps S112 through S124 are performed according to the first embodiment;

DETAILED DESCRIPTION

Figure 1:
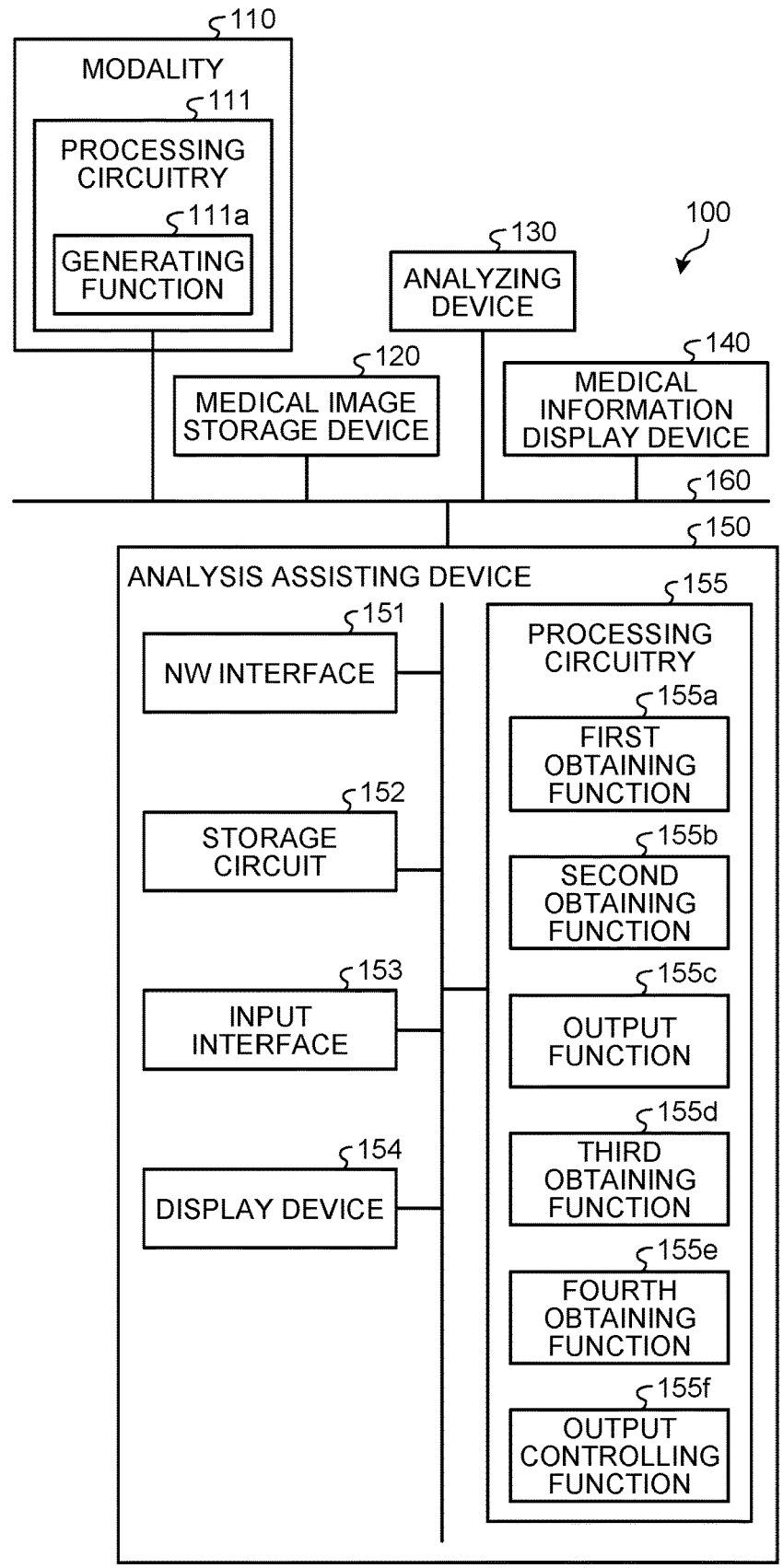
FIG. 1 is a diagram illustrating exemplary configurations of an analysis assisting system and an analysis assisting device according to a first embodiment.

One of the problems to be solved by the embodiments disclosed in the present specification and drawings is to enhance precision levels of analysis results. However, possible problems to be solved by the embodiments disclosed in the present specification and drawings are not limited to the abovementioned problem. It is also acceptable to consider problems corresponding to advantageous effects achieved by various configurations described in the following embodiments as other problems.

An analysis assisting device according to an embodiment includes processing circuitry. The processing circuitry is configured to obtain first analysis image data obtained on the basis of an image taken of a patient and additional information of the image. The processing circuitry is configured to obtain an analysis result of analyzing the first analysis image data. When the analysis result does not satisfy a predetermined condition, the processing circuitry is configured to output an image processing condition optimal for the analysis. The processing circuitry is configured either to obtain second analysis image data by generating the second analysis image data by performing an image processing process on the basis of the image processing condition; or to obtain the second analysis image data generated as a result of an external device performing an image processing process on the basis of the image processing condition. The processing circuitry is configured to obtain an analysis result of analyzing the second analysis image data.

In the following sections, exemplary embodiments and modification examples of an analysis assisting device, an analysis assisting system, and a program will be explained in detail, with reference to the accompanying drawings. It is possible to combine any of the embodiments with one or more conventional techniques, any of the modification examples, and/or any of the other embodiments, as long as no conflict occurs therebetween. Similarly, it is possible to combine any of the modification examples with one or more conventional techniques, any of the embodiments, and/or any of the other modification examples, as long as no conflict occurs therebetween. Further, in the description below, some of the constituent elements that are the same as each other will be referred to by using the same reference characters, and duplicate explanations thereof may be omitted.

First Embodiment

FIG. 1 is a diagram illustrating exemplary configurations of an analysis assisting system 100 and an analysis assisting device 150 according to a first embodiment. For example, as illustrated in FIG. 1, the analysis assisting system 100 according to the first embodiment includes a modality 110, a medical image storage device 120, an analyzing device 130, a medical information display device 140, and the analysis assisting device 150. In this situation, the modality 110, the medical image storage device 120, the analyzing device 130, the medical information display device 140, and the analysis assisting device 150 are communicably connected together via a network 160. The analysis assisting system 100 according to the present embodiment is installed in a medical facility such as a hospital or a clinic.

The modality 110 is, for example, a medical image generating device configured to generate medical image data, such as an X-ray Computed Tomography (CT) apparatus, a Magnetic Resonance Imaging (MRI) apparatus, an ultrasound diagnosis apparatus, a Positron Emission Tomography (PET) apparatus, or a Single Photon Emission Computed Tomography (SPECT) apparatus. For example, the modality 110 is configured to image a site of a patient (an examined subject) subject to an analysis and to generate image data (medical image data) rendering the site of the patient subject to the analysis. The site subject to the analysis may be any of various sites such as the lungs or the heart.

In the following sections, an example will be explained in which the modality 110 is an X-ray CT apparatus. In this situation, the modality 110 includes processing circuitry 111. The processing circuitry 111 is realized by using a processor, for example. The processing circuitry 111 includes a generating function 111*a*. In this situation, for example, the generating function 111*a*, which is a constituent element of the processing circuitry 111 illustrated in FIG. 1, is stored in a storage circuit included in the modality 110, while taking the form of a computer-executable program. The processing circuitry 111 is configured to realize the generating function 111*a* corresponding to the program, by reading the program from the storage circuit and executing the read program. In other words, the processing circuitry 111 that has read the program includes the generating function 111*a* illustrated within the processing circuitry 111 in FIG. 1. The generating function 111*a* is an example of a generating unit.

The modality 110 being the X-ray CT apparatus is configured to acquire detection data expressing a distribution of X-rays that have passed through the patient, by moving an X-ray tube and an X-ray detector so as to rotate on a circular path surrounding the patient. Further, on acquired projection data, the generating function 111*a* of the modality 110 is configured to perform pre-processing processes such as a logarithmic conversion process, an offset correction process, an inter-channel sensitivity correction process, a beam hardening correction, and/or the like. The data resulting from the pre-processing processes may be referred to as raw data. The detection data before the pre-processing processes and the raw data resulting from the pre-processing processes may collectively be referred to as the projection data. Further, the generating function 111*a* is configured to generate CT image data (image data) by performing reconstruction (a reconstruction process) using a filter backprojection method or a successive approximation reconstruction method on the raw data resulting from the pre-processing processes, on the basis of predetermined image processing conditions. In this situation, the image processing conditions include a reconstructing condition and various types of parameters used at the time of generating the image data. The reconstructing condition includes a reconstruction mathematical function used at the time of performing the reconstruction. Further, on the basis of an input operation received from a user via an input interface included in the modality 110, predetermined image processing conditions, and the like, the generating function 111*a* is configured to convert the CT image data into image data such as tomographic image data on an arbitrary cross-sectional plane or three-dimensional image data by using a publicly-known method. In this manner, the generating function 111*a* is configured to generate the image data. Further, the generating function 111*a* is configured to generate DICOM data including image data and various types of additional information (tags). The image data included in the DICOM data may be the CT image data or may be the image data such as the tomographic image data or the three-dimensional image data.

After that, the modality 110 is configured to transmit the image data to the medical image storage device 120 via the network 160.

In this situation, when causing the analyzing device 130 to perform an analysis on the subject of the analysis, the user inputs an instruction to the modality 110 via an input interface included in the modality 110, instructing that the raw data rendering the site subject to the analysis or the DICOM data including the image data rendering the site subject to the analysis be transmitted to the analysis assisting device 150. When the instruction is input to the modality 110, the modality 110 is configured, on the basis of the input instruction, to transmit the raw data rendering the site subject to the analysis or the DICOM data including the image data rendering the site subject to the analysis, to the analysis assisting device 150.

The medical image storage device 120 is configured to store therein various types of image data. More specifically, the medical image storage device 120 is configured to obtain the image data from the modality 110 via the network 160 and to store and save the obtained image data into a storage circuit included in the medical image storage device 120. For example, the medical image storage device 120 is realized by using a computer device such as a server or a workstation. Further, for example, the medical image storage device 120 is realized by using a Picture Archiving and Communication System (PACS) or the like and is configured to store therein the image data in a format compliant with DICOM.

The analyzing device 130 is configured to execute an analysis application for analyzing the site subject to the analysis and obtaining an analysis result. For example, the analyzing device 130 is configured to receive the DICOM data transmitted thereto by the analysis assisting device 150, to input the received DICOM data to the analysis application, and to execute the analysis application. The analysis application is configured to analyze the site subject to the analysis rendered in the image data included in the input DICOM data and to output the analysis result. For instance, an example will be explained in which DICOM data including image data rendering the lungs as the site subject to the analysis is input to an analysis application for analyzing the bronchi (hereinafter, "bronchi analysis application"). In this situation, the bronchi analysis application is configured, for example, to perform an analysis for identifying a region having bronchitis from a lungs region and to further output the identified region as an analysis result. Alternatively, the bronchi analysis application may be configured, for example, to perform an analysis to segment (extract) a bronchi region from the lungs region and to further output the segmented bronchi region as an analysis result. After that, the analyzing device 130 is configured to obtain the analysis result output by the analysis application. Subsequently, the analyzing device 130 is configured to transmit the obtained analysis result to the analysis assisting device 150 via the network 160. The analyzing device 130 is realized by using a computer device such as a server or a workstation.

In this situation, when the entire region of the lungs is not rendered in the image data included in the input DICOM data, the bronchi analysis application is not able to perform the analysis and thus outputs an error indicating that the entire region of the lungs is not rendered, as the analysis result. In other words, the bronchi analysis application is configured to output the error as the analysis result, when only a partial region from the entire region of the lungs is rendered in the image data included in the input DICOM data. After that, the analyzing device 130 is configured to obtain the error output by the analysis application. Subsequently, the analyzing device 130 is configured to transmit the obtained error as the analysis result to the analysis assisting device 150 via the network 160.

The medical information display device 140 is configured to display various types of medical information related to the patient. More specifically, the medical information display device 140 is configured to obtain medical information such as the analysis result from the analysis assisting device 150 via the network 160 and to cause a display device included in the medical information display device 140 to display the obtained medical information. For example, the medical information display device 140 is realized by using a computer device such as a workstation, a personal computer, or a tablet terminal.

The analysis assisting device 150 is configured to assist the analysis performed by the analyzing device 130 so as to enhance the precision level of the analysis result. More specifically, the analysis assisting device 150 is configured to obtain the raw data or the DICOM data from the modality 110 via the network 160 and to perform various types of processes on the obtained raw data or DICOM data. For example, the analysis assisting device 150 is realized by using a computer device such as a server or a workstation.

As illustrated in FIG. 1, the analysis assisting device 150 includes a network (NW) interface 151, a storage circuit 152, an input interface 153, a display device 154, and processing circuitry 155.

The NW interface 151 is configured to control communication and transfer of various types of data transmitted and received between the analysis assisting device 150 and other devices (the modality 110, the medical image storage device 120, and the medical information display device 140) connected to the analysis assisting device 150 via the network 160. More specifically, the NW interface 151 is connected to the processing circuitry 155 and is configured to receive the data or the like transmitted from any of the other devices and to transmit the received data or the like to the processing circuitry 155. Also, the NW interface 151 is configured to receive the data or the like transmitted from the processing circuitry 155 and to transmit the received data or the like to any of the other devices. For example, the NW interface 151 is realized by using a network card, a network adaptor, a Network Interface Controller (NIC), or the like.

The storage circuit 152 is configured to store therein various types of data and various types of programs. More specifically, the storage circuit 152 is connected to the processing circuitry 155 and is configured to store therein the various types of data under control of the processing circuitry 155. Further, the storage circuit 152 also has a function of a work memory configured to temporarily save therein various types of data used in processes performed by the processing circuitry 155. For example, the storage circuit 152 is realized by using a semiconductor memory element such as a Random Access Memory (RAM) or a flash memory, or a hard disk, an optical disk, or the like.

The input interface 153 is configured to receive operations to input various types of instructions and various types of information from a user of the analysis assisting system 100. More specifically, the input interface 153 is connected to the processing circuitry 155 and is configured to convert the input operations received from the user into electrical signals and to transmit the electrical signals to the processing circuitry 155. For example, the input interface 153 is realized by using a trackball, a switch button, a mouse, a keyboard, a touchpad on which input operations can be performed by touching an operation surface thereof, a touch screen in which a display screen and a touchpad are integrally formed, a contactless input interface using an optical sensor, an audio input interface, and/or the like. In the present disclosure, the input interface 153 does not necessarily have to include physical operation component parts such as a mouse, a keyboard, and/or the like. For instance, possible examples of the input interface 153 include electrical signal processing circuitry configured to receive an electrical signal corresponding to an input operation from an external input device provided separately from the analysis assisting device 150 and to transmit the electrical signal to the processing circuitry 155. The processing circuitry in this situation is realized by using a processor, for example. The input interface 153 is an example of a receiving unit.

The display device 154 is configured to display various types of images, various types of information, and various types of data. More specifically, the display device 154 is connected to the processing circuitry 155 and is configured to display images based on various types of image data received from the processing circuitry 155, the various types of information, and the various types of data. For example, the display device 154 is realized by using a liquid crystal monitor, a Cathode Ray Tube (CRT) monitor, a touch panel, or the like. The display device 154 is an example of a display unit.

The processing circuitry 155 is configured to control the entirety of the analysis assisting device 150. For example, the processing circuitry 155 is configured to perform various types of processes in response to the input operations received from the user via the input interface 153. Further, for example, the processing circuitry 155 is configured to receive, via the NW interface 151, the raw data or the DICOM data transmitted by the modality 110 and to further store the received raw data or DICOM data into the storage circuit 152. The raw data or the DICOM data stored in the storage circuit 152 is used in the process illustrated in FIG. 2 (explained later). The processing circuitry 155 is realized by using a processor, for example.

The exemplary configurations of the analysis assisting system 100 and the analysis assisting device 150 according to the present embodiment have thus been explained. According to the present embodiment, the analysis assisting system 100 and the analysis assisting device 150 are configured to perform the various types of processes described below so that it is possible to enhance the precision level of the analysis result obtained from the analysis performed by the analyzing device 130.

For example, as illustrated in FIG. 1, the processing circuitry 155 includes a first obtaining function 155a, a second obtaining function 155b, an output function 155c, a third obtaining function 155d, a fourth obtaining function 155e, and an output controlling function 155f. The first obtaining function 155a is an example of a first obtaining unit. The second obtaining function 155b is an example of a second obtaining unit. The output function 155c is an example of an output unit. The third obtaining function 155d is an example of a third obtaining unit. The fourth obtaining function 155e is an example of a fourth obtaining unit. The output controlling function 155f is an example of an output controlling unit.

In this situation, for example, processing functions of the constituent elements of the processing circuitry 155 illustrated in FIG. 1, namely, the first obtaining function 155a, the second obtaining function 155b, the output function 155c, the third obtaining function 155d, the fourth obtaining function 155e, and the output controlling function 155f are stored in the storage circuit 152 in the form of computer-executable programs. The processing circuitry 155 is configured to realize the functions corresponding to the programs, by reading the programs from the storage circuit 152 and executing the read programs. In other words, the processing circuitry 155 that has read the programs has the functions illustrated within the processing circuitry 155 in FIG. 1.

Figure 2:
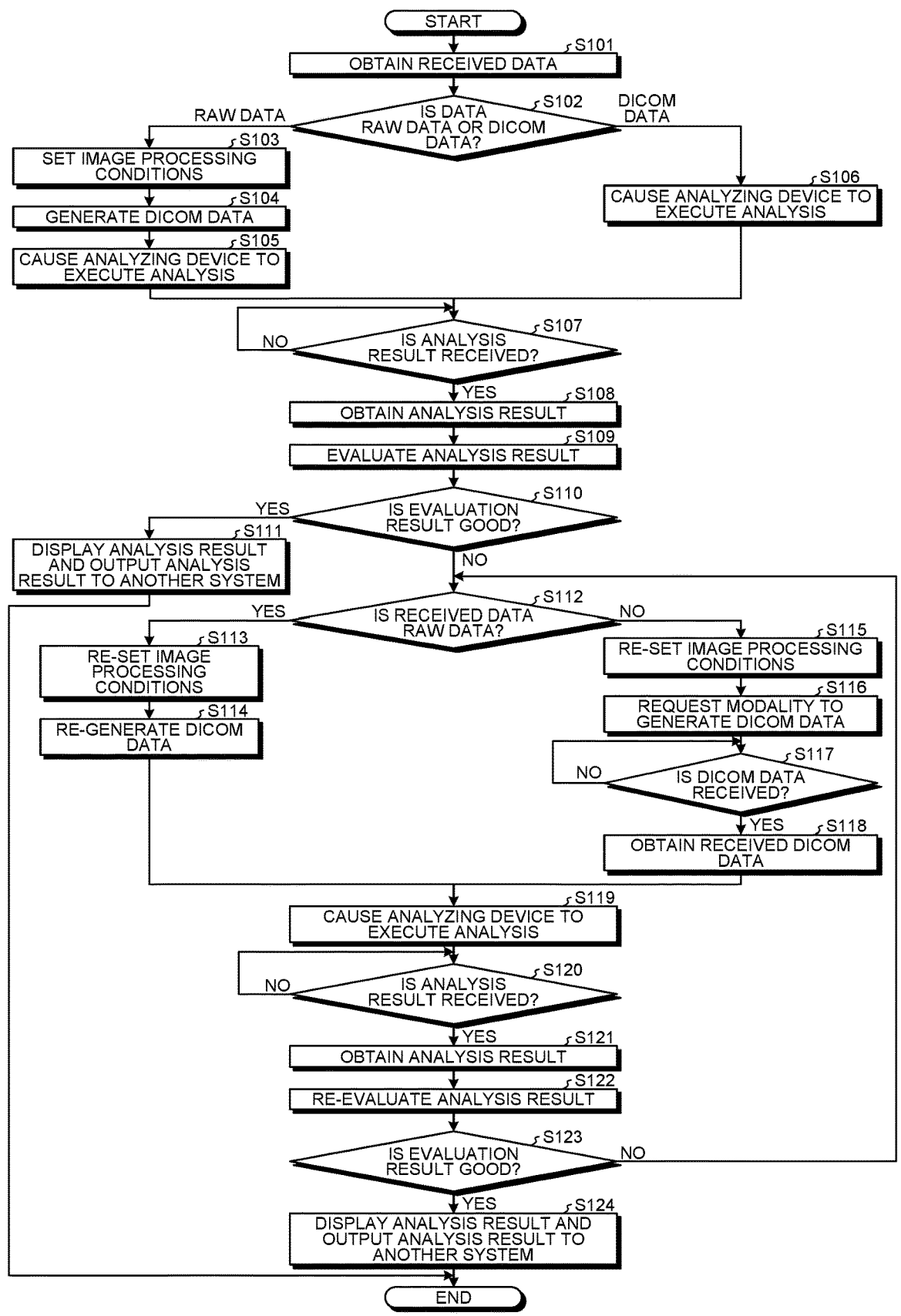
FIG. 2 is a flowchart illustrating a flow in an example of an analysis assisting process performed by the analysis assisting device according to the first embodiment.

FIG. 2 is a flowchart illustrating a flow in an example of an analysis assisting process performed by the analysis assisting device 150 according to the first embodiment. For example, the analysis assisting process is performed when raw data or DICOM data is received by the analysis assisting device 150, and the received raw data or DICOM data is further stored in the storage circuit 152.

As illustrated in FIG. 2, the first obtaining function 155a obtains the raw data or the DICOM data stored in the storage circuit 152 (step S101). After that, the first obtaining function 155a judges whether the data obtained at step S101 is raw data or DICOM data (step S102).

When the data obtained at step S101 is raw data (step S102: RAW DATA), the first obtaining function 155a sets image processing conditions (step S103).

After that, on the basis of the image processing conditions set at step S103, the first obtaining function 155a generates DICOM data (step S104). A specific example of the process at step S104 will be explained. For example, on the basis of the image processing conditions set at step S103, the first obtaining function 155a generates CT image data, by reconstructing the raw data obtained at step S101. After that, on the basis of the CT image data and additional information of the CT image data, the first obtaining function 155a generates the DICOM data including the CT image data and the additional information thereof. In this situation, the first obtaining function 155a may convert the CT image data into image data such as tomographic image data on an arbitrary cross-sectional plane or three-dimensional image data by using a publicly-known method, so as to generate the DICOM data including the image data and the additional information of the image data, on the basis of the image data and the additional information thereof. In this manner, at step S104, the first obtaining function 155a obtains the DICOM data based on the image data taken of the patient and the additional information of the image data. The DICOM data obtained at step S104 is an example of the first analysis image data.

After that, the second obtaining function 155b transmits the DICOM data obtained at step S104 to the analyzing device 130 and further causes the analyzing device 130 to execute the analysis application and to transmit an analysis result to the analysis assisting device 150 (step S105). After that, the second obtaining function 155b proceeds to step S107.

Next, the situation where, on the contrary, the data obtained at step S101 is DICOM data (step S102: DICOM DATA) will be explained. In this situation, at step S101, the first obtaining function 155a obtains the DICOM data based on the image data taken of the patient and the additional information of the image data. The DICOM data obtained at step S101 in this manner is an example of the first analysis image data. After that, the second obtaining function 155b transmits the DICOM data obtained at step S101 to the analyzing device 130 and further causes the analyzing device 130 to execute the analysis application and to transmit an analysis result to the analysis assisting device 150 (step S106).

After that, the second obtaining function 155b judges whether or not the analysis result transmitted by the analyzing device 130 is received (step S107). When the analysis result is not received (step S107: No), the second obtaining function 155b again performs the judging process at step S107. On the contrary, when the analysis result is received (step S107: Yes), the second obtaining function 155b obtains the received analysis result (step S108). In other words, at step S108, the second obtaining function 155b obtains the analysis result of analyzing the DICOM data obtained at step S101 or step S104.

After that, the output function 155c evaluates the analysis result (step S109). For example, at step S109, the output function 155c judges whether or not the analysis result presents the abovementioned error. After that, the output function 155c judges whether or not a result of the evaluation is good (step S110).

A specific example of the processes at steps S109 and S110 will be explained. In the present example, a situation in which the analyzing device 130 has performed the analysis by using the bronchi analysis application will be explained. In this situation, the analysis result presents one of the following: a region having bronchitis; the bronchi region resulting from segmentation; and the error indicating that the entire region of the lungs is not rendered.

Further, at step S110, when the analysis result presents the error, the output function 155c determines that the evaluation result is not good. In contrast, when the analysis result presents a region having bronchitis or the bronchi region resulting from the segmentation, the output function 155c determines that the evaluation result is good. In this manner, at step S110, the output function 155c judges whether or not the analysis result satisfies the predetermined condition. In this situation, when the analysis result presents either the region having bronchitis or the bronchi region resulting from the segmentation, the analysis result is determined to satisfy the predetermined condition. On the contrary, when the analysis result presents the error, the analysis result is determined not to satisfy the predetermined condition.

The time period during which the processes at steps S101 through S110 are performed is the time period during which the processes are performed on the received raw data or DICOM data after the reception of the raw data or the DICOM data is completed. Thus, while the processes at steps S101 through S110 are performed, the analysis assisting device 150 is configured to output a message indicating that the reception of the raw data or the DICOM data is completed and that the processes are performed on the received raw data or DICOM data. FIG. 3 is a drawing illustrating an example of the message displayed while the processes at steps S101 through S110 are performed according to the first embodiment. For example, while the processes at steps S101 through S110 are performed, the output controlling function 155f is configured to exercise control so that the message "RECEPTION IS COMPLETED; EXECUTION IS UNDERWAY" illustrated in FIG. 3 is output. The message "RECEPTION IS COMPLETED; EXECUTION IS UNDERWAY" illustrated in FIG. 3 is a message indicating that the reception of the raw data or the DICOM data is completed and that the processes are performed on the received raw data or DICOM data. More specifically, the output controlling function 155f is configured to cause the display device 154 to display the message "RECEPTION IS COMPLETED; EXECUTION IS UNDERWAY" illustrated in FIG. 3. As a result, the user is able to understand that the reception of the raw data or the DICOM data is completed and that the processes are performed on the received raw data or DICOM data.

When the evaluation result is good (step S110: Yes), the output controlling function 155f exercises control so that the analysis result and a message indicating completion of the analysis are output (step S111), and the analysis assisting process is thus ended. FIG. 4 is a drawing illustrating examples of the message and the analysis result output at step S111 according to the first embodiment. For example, at step S111, the output controlling function 155f causes the display device 154 to display the message "ANALYSIS IS COMPLETED" illustrated in FIG. 4 together with the analysis result illustrated in FIG. 4. The message "ANALYSIS IS COMPLETED" illustrated in FIG. 4 is a message indicating that the analysis is completed. As a result, the user is able to understand the analysis result and that the analysis is completed.

Further, at step S111, the output controlling function 155f transmits the message "ANALYSIS IS COMPLETED" illustrated in FIG. 4 together with the analysis result illustrated in FIG. 4 to the medical information display device 140 via the network 160. Accordingly, the medical information display device 140 causes a display device included in the medical information display device 140 to display the message "ANALYSIS IS COMPLETED" illustrated in FIG. 4, together with the analysis result illustrated in FIG. 4.

On the contrary, when the evaluation result is not good (step S110: No), the output controlling function 155f judges whether or not the data obtained at step S101 is raw data (step S112). At step S112, when it is determined that the obtained data is not raw data, it means that the obtained data is DICOM data.

When the data obtained at step S101 is raw data (step S112: Yes), the output function 155c re-sets image processing conditions (step S113). A specific example of the process at step S113 will be explained. For example, at step S113, the evaluation result presents the error, while the obtained data is raw data. Accordingly, the entire region of the lungs is not rendered in the image data included in the DICOM data analyzed by the analyzing device 130. For this reason, at step S113, the output function 155c detects the lungs region from the raw data. After that, the output function 155c changes the size of a region to be reconstructed (a reconstruction region) so that the size of the reconstruction region included in the most up-to-date image processing conditions includes the detected lungs region and thus newly sets the changed image processing conditions.

After that, the third obtaining function 155d generates DICOM data on the basis of the most up-to-date image processing conditions set at step S113 (step S114), and the process proceeds to step S119. Next, a specific example of the process at step S114 will be explained. For example, the third obtaining function 155d generates the CT image data by reconstructing the raw data obtained at step S101, on the basis of the most up-to-date image processing conditions set at step S113. After that, on the basis of the CT image data and additional information of the CT image data, the third obtaining function 155d generates the DICOM data including the CT image data and the additional information thereof. In this situation, the third obtaining function 155d may convert the CT image data into image data such as tomographic image data on an arbitrary cross-sectional plane or three-dimensional image data by using a publicly-known method so as to generate DICOM data including the image data and additional information of the image data, on the basis of the image data and the additional information thereof. As explained herein, at step S114, the third obtaining function 155d obtains the DICOM data based on the image data taken of the patient and the additional information of the image data. The DICOM data obtained at step S114 is an example of the second analysis image data or the third analysis image data.

On the contrary, when the data obtained at step S101 is not raw data (step S112: No), i.e., when the data obtained at step S101 is DICOM data, the output function 155c re-sets image processing conditions (step S115). Next, a specific example of the process at step S115 will be explained. For example, at step S115, the evaluation result presents the error, while the obtained data is DICOM data. Accordingly, the image data included in the DICOM data analyzed by the analyzing device 130 does not render the entire region of the lungs. For this reason, at step S115, the output function 155c changes the size of a region to be reconstructed (a reconstruction region) so that the size of the reconstruction region included in the most up-to-date image processing conditions is enlarged in a predetermined direction in a predetermined amount and thus newly sets the changed image processing conditions.

After that, the third obtaining function 155d controls the NW interface 151 so as to transmit, to the modality 110, an instruction that DICOM data be generated on the basis of the most up-to-date image processing conditions set at step S115 (step S116). Accordingly, the NW interface 151 transmits, to the modality 110, the instruction that the DICOM data be generated on the basis of the most up-to-date image processing conditions. In this situation, the instruction includes the most up-to-date image processing conditions.

When the modality 110 receives the instruction, the generating function 111a is configured to automatically generate the DICOM data according to the instruction. For example, the generating function 111a is configured to generate CT image data by reconstructing, on the basis of the most up-to-date image processing conditions, the raw data used at the time of generating the image data included in the DICOM data that has already been transmitted to the analysis assisting device 150. Further, on the basis of the CT image data and additional information of the CT image data, the generating function 111a is configured to generate the DICOM data including the CT image data and the additional information thereof. In this situation, the generating function 111a may convert the CT image data into image data such as tomographic image data on an arbitrary cross-sectional plane or three-dimensional image data by using a publicly-known method so as to generate DICOM data including the image data and additional information of the image data, on the basis of the image data and the additional information thereof. As described herein, at step S116, the generating function 111a generates the DICOM data based on the image data taken of the patient and the additional information of the image data. The DICOM data generated at step S116 is an example of the second analysis image data or the third analysis image data.

Alternatively, the modality 110 may be configured to generate the DICOM data, not automatically but by receiving an operation performed by the user. For example, the modality 110 may cause a display device included in the modality 110 to display the image processing conditions included in the received instruction. The user checks the displayed image processing conditions and changes the image processing conditions, as necessary, via the input interface included in the modality 110. After that, upon receipt of an instruction input by the user via the input interface instructing that the DICOM data be generated, the generating function 111a is configured to generate, on the basis of the image processing conditions, the DICOM data by using a method similar to the abovementioned method for generating the DICOM data automatically.

After that, the modality 110 is configured to transmit the generated DICOM data to the analysis assisting device 150 via the network 160.

The third obtaining function 155d judges whether or not the DICOM data transmitted by the modality 110 is received (step S117). When the DICOM data is not received (step S117: No), the third obtaining function 155d again performs the judging process at step S117.

On the contrary, when the DICOM data is received (step S117: Yes), the third obtaining function 155d obtains the received DICOM data (step S118). The DICOM data obtained at step S118 is an example of the second analysis image data or the third analysis image data.

After that, the fourth obtaining function 155e transmits, to the analyzing device 130, the DICOM data obtained at step S114 or step S118 and further causes the analyzing device 130 to execute the analysis application and to transmit the analysis result to the analysis assisting device 150 (step S119).

After that, the fourth obtaining function 155e judges whether or not the analysis result transmitted by the analyzing device 130 is received (step S120). When the analysis result is not received (step S120: No), the fourth obtaining function 155e again performs the judging process at step S120. On the contrary, when the analysis result is received (step S120: Yes), the fourth obtaining function 155e obtains the received analysis result (step S121). In other words, at step S121, the fourth obtaining function 155e obtains the analysis result of analyzing the DICOM data obtained at step S114 or step S118.

After that, the output function 155c again evaluates the analysis result (step S122). The method for evaluating the analysis result at step S122 may be, for example, the same as the method for evaluating the analysis result at step S109. Further, the output function 155c judges whether or not the evaluation result is good (step S123). The method for judging whether or not the evaluation result is good at step S123 may be, for example, the same as the method for judging whether or not the evaluation result is good at step S110.

When the evaluation result is not good (step S123: No), the output function 155c returns to step S112 so as to perform the processes at step S112 and the steps thereafter.

On the contrary, when the evaluation result is good (step S123: Yes), the output controlling function 155f exercises control so that the analysis result and a message indicating completion of the analysis are output, similarly to the process at step S111 (step S124), and the analysis assisting process is thus ended.

The processes at steps S112 through S123 are repeatedly performed until the evaluation result is determined to be good at step S123. Accordingly, when the evaluation result is determined to be good at step S123, the most up-to-date image processing conditions set at step S113 or step S115 are image processing conditions optimal for the analysis of the image. Consequently, the output function 155c is configured to output the image processing conditions optimal for the analysis, when the analysis result does not satisfy the predetermined condition.

Further, in the processes at steps S112 through S118, the third obtaining function 155d is configured either to obtain the DICOM data (the second analysis image data) by generating the DICOM data by performing the image processing process on the basis of the optimal image processing conditions; or to obtain the DICOM data (the second analysis image data) generated as a result of the modality 110 performing the image processing process on the basis of the optimal image processing conditions.

After that, in the processes at steps S119 through S121, the fourth obtaining function 155e is configured to obtain the analysis result of analyzing the image data included in the DICOM data generated on the basis of the optimal image processing conditions.

Further, as explained above, the processes at steps S112 through S123 are repeatedly performed until the evaluation result is determined to be good at step S123. Accordingly, when the analysis result of analyzing the DICOM data obtained at step S101 or step S104 does not satisfy the predetermined condition, the output function 155c is configured to repeatedly change the image processing conditions until the analysis result of analyzing the DICOM data newly obtained at step S114 or step S118 satisfies the predetermined condition. The DICOM data newly obtained at step S114 or step S118 is an example of the third analysis image data.

Every time the image processing conditions are changed, the third obtaining function 155d is configured either to obtain the DICOM data by generating the DICOM data on the basis of the changed image processing conditions at step S114; or to obtain the DICOM data generated as a result of the modality 110 performing the image processing process on the basis of the changed image processing conditions at step S118.

The time period during which the processes at steps S112 through S124 are performed is the time period during which re-processing is performed where the reconstruction is performed on the raw data again, the DICOM data is obtained again, and the analysis is performed again. The processes at steps S113 and S115 are the processes to change the image processing conditions. The processes at steps S114 and S116 through S118 are the processes to obtain the DICOM data. The processes at steps S119 through S121 are the processes to obtain the analysis result of analyzing the DICOM data.

Accordingly, while the processes at steps S112 through S124 are performed, the analysis assisting device 150 is configured to output a message indicating that the reconstruction is being performed and that the re-analysis is underway. Further, while the processes at steps S112 through S124 are performed, the analysis assisting device 150 is configured to output a message indicating that a process for performing the re-processing is underway. In addition, while the processes at steps S112 through S124 are performed, the analysis assisting device 150 is configured to output a message indicating that the analysis using the initial (first) image processing conditions failed. Furthermore, while the processes at steps S112 through S124 are performed, the analysis assisting device 150 is configured to output the image processing conditions to be used for the re-processing.

FIG. 5 is a drawing illustrating an example of the message displayed while the processes at steps S112 through S124 are performed according to the first embodiment. For example, while the processes at steps S112 through S124 are performed, the output controlling function 155f is configured to exercise control so that the message "RECONSTRUCTION AND RE-ANALYSIS ARE UNDERWAY" illustrated in FIG. 5 is output. The message "RECONSTRUCTION AND RE-ANALYSIS ARE UNDERWAY" is a message indicating that the reconstruction is being performed and the re-analysis is underway. More specifically, the output controlling function 155f causes the display device 154 to display the message "RECONSTRUCTION AND RE-ANALYSIS ARE UNDERWAY". As a result, the user is able to understand that the reconstruction is being performed and that the re-analysis is underway. The display device 154 configured to output the message "RECONSTRUCTION AND RE-ANALYSIS ARE UNDERWAY" is an example of a message output unit.

Further, while the processes at steps S112 through S124 are performed, the output controlling function 155f is configured to exercise control so that the message "PROCESS FOR PERFORMING RE-PROCESSING IS UNDERWAY" illustrated in FIG. 5 is output. The message "PROCESS FOR PERFORMING RE-PROCESSING IS UNDERWAY" is a message indicating that the process for performing the re-processing is underway. More specifically, the output controlling function 155f is configured to cause the display device 154 to display the message "PROCESS FOR PERFORMING RE-PROCESSING IS UNDERWAY". As a result, the user is able to understand that the process for performing the re-processing is underway. The display device 154 configured to display the message "PROCESS FOR PERFORMING RE-PROCESSING IS UNDERWAY" is an example of a message output unit.

Further, while the processes at steps S112 through S124 are performed, the output controlling function 155f is configured to exercise control so that the message "ANALYSIS USING INITIAL (FIRST) IMAGE PROCESSING CONDITIONS FAILED" illustrated in FIG. 5 is output. The message "ANALYSIS USING INITIAL (FIRST) IMAGE PROCESSING CONDITIONS FAILED" is a message indicating that the analysis using the initial (first) image processing conditions failed. More specifically, the output controlling function 155f is configured to cause the display device 154 to display the message "ANALYSIS USING INITIAL (FIRST) IMAGE PROCESSING CONDITIONS FAILED". As a result, the user is able to understand that the analysis using the initial image processing conditions failed. The display device 154 configured to output the message "ANALYSIS USING INITIAL (FIRST) IMAGE PROCESSING CONDITIONS FAILED" is an example of a message output unit.

Further, while the processes at steps S112 through S124 are performed, the output controlling function 155f is configured to exercise control so that the text "IMAGE PROCESSING CONDITIONS TO BE USED IN RE-PROCESSING: AA, BB, . . . " illustrated in FIG. 5 is output. The "IMAGE PROCESSING CONDITIONS TO BE USED IN RE-PROCESSING: AA, BB, . . . " are the changed image processing conditions to be used in the re-processing. More specifically, the output controlling function 155f is configured to cause the display device 154 to display the text "IMAGE PROCESSING CONDITIONS TO BE USED IN RE-PROCESSING: AA, BB, . . . ". As a result, the user is able to understand the changed image processing conditions to be used in the re-processing. The display device 154 configured to output the text "IMAGE PROCESSING CONDITIONS TO BE USED IN RE-PROCESSING: AA, BB, . . . " is an example of an image processing condition output unit.

The analysis assisting system 100 and the analysis assisting device 150 according to the first embodiment have thus been explained. The analysis assisting system 100 and the analysis assisting device 150 are configured to repeatedly change the image processing conditions until no error is output. Further, the analysis assisting system 100 and the analysis assisting device 150 are configured to output the analysis result corresponding to the situation where the error is no longer output. Consequently, the analysis assisting system 100 and the analysis assisting device 150 are able to enhance the precision level of the analysis result.

Further, the analysis assisting system 100 and the analysis assisting device 150 are configured to automatically obtain the DICOM data or to cause the modality 110 to generate the DICOM data automatically. In those situations, because the analysis assisting system 100 and the analysis assisting device 150 are configured to obtain the DICOM data without requesting the user to set the image processing conditions, it is possible to alleviate the trouble for the user at the time of obtaining the DICOM data.

Further, the analysis assisting system 100 and the analysis assisting device 150 are configured to cause the modality 110 to generate the DICOM data, not automatically but by receiving the operation performed by the user. For example, the modality 110 is configured to cause the image processing conditions included in the received instruction to be displayed on the display device included in the modality 110. The user checks the displayed image processing conditions and changes the image processing conditions, as necessary, via the input interface included in the modality 110. Further, upon receipt of the instruction input by the user via the input interface instructing that the DICOM data be generated, the modality 110 is configured to generate the DICOM data on the basis of the image processing conditions. In this situation, although the analysis assisting system 100 and the analysis assisting device 150 request the user to set the image processing conditions, because the image processing conditions are presented to the user, it is possible to alleviate the trouble for the user at the time of determining the image processing conditions.

Further, although the example was explained in which the analyzing device 130 is configured to execute the single analysis application, the analyzing device 130 may be configured to execute a plurality of types of analysis applications. Thus, an example will be explained in which the analyzing device 130 is configured to execute the plurality of types of analysis applications. In the present example, a situation will be explained in which the analyzing device 130 is configured to execute the plurality of types of analysis applications to analyze the head.

Upon receipt of a piece of raw data rendering the head or a piece of DICOM data including image data rendering the head, the analysis assisting device 150 is configured to output the one piece of raw data or the one piece of DICOM data that was received to the analyzing device 130. In this situation, the analyzing device 130 is configured to execute the plurality of types of analysis applications by using the one piece of raw data or the one piece of DICOM data and to further transmit a plurality of analysis results regarding the head to the analysis assisting device 150. Subsequently, with respect to each of the analysis applications, the analysis assisting device 150 is configured to output image processing conditions optimal for the analysis. After that, with respect to each of the analysis applications, the analysis assisting device 150 is configured to obtain DICOM data on the basis of the image processing conditions optimal for the analysis. In other words, with respect to each of the analysis applications, the analysis assisting device 150 is configured to generate the DICOM data optimal for the analysis performed by the analysis application. Accordingly, the analysis assisting system 100 and the analysis assisting device 150 are able to make available the plurality of pieces of data (a group of data) which render the subject of the analysis in mutually the same site (i.e., the head) and on which the plurality of types of analysis applications are able to perform the analyses.

First Modification Example of First Embodiment

The analysis application may include a plurality of applications, while the analyzing device 130 may be configured to sequentially execute the plurality of applications included in the analysis application. Further, when the evaluation result is determined to be not good at step S110 or step S123, the analysis assisting device 150 may be configured to predict, before the analysis result is re-evaluated at step S122, whether or not the evaluation result is to be good on the basis of the DICOM data obtained at step S114 or step S118. After that, in accordance with a result of the prediction, the analysis assisting device 150 may be configured to determine the types of applications included in the analysis application to be executed by the analyzing device 130. Thus, the following will explain this modification example as a first modification example of the first embodiment. In the description of the first modification example of the first embodiment, differences from the first embodiment will primarily be explained. The explanations of some of the elements that are the same as those in the first embodiment may be omitted.

To begin with, in the first modification example of the first embodiment, the analyzing device 130 is configured to sequentially execute the plurality of applications included in the analysis application. For example, the analysis application incudes a noise reduction application to reduce noise in image data; a body movement correction application to correct body movements; and a segmentation application to segment the bronchi. Further, the analyzing device 130 executes the noise reduction application, then executes the body movement correction application, before executing the segmentation application.

Figure 6:
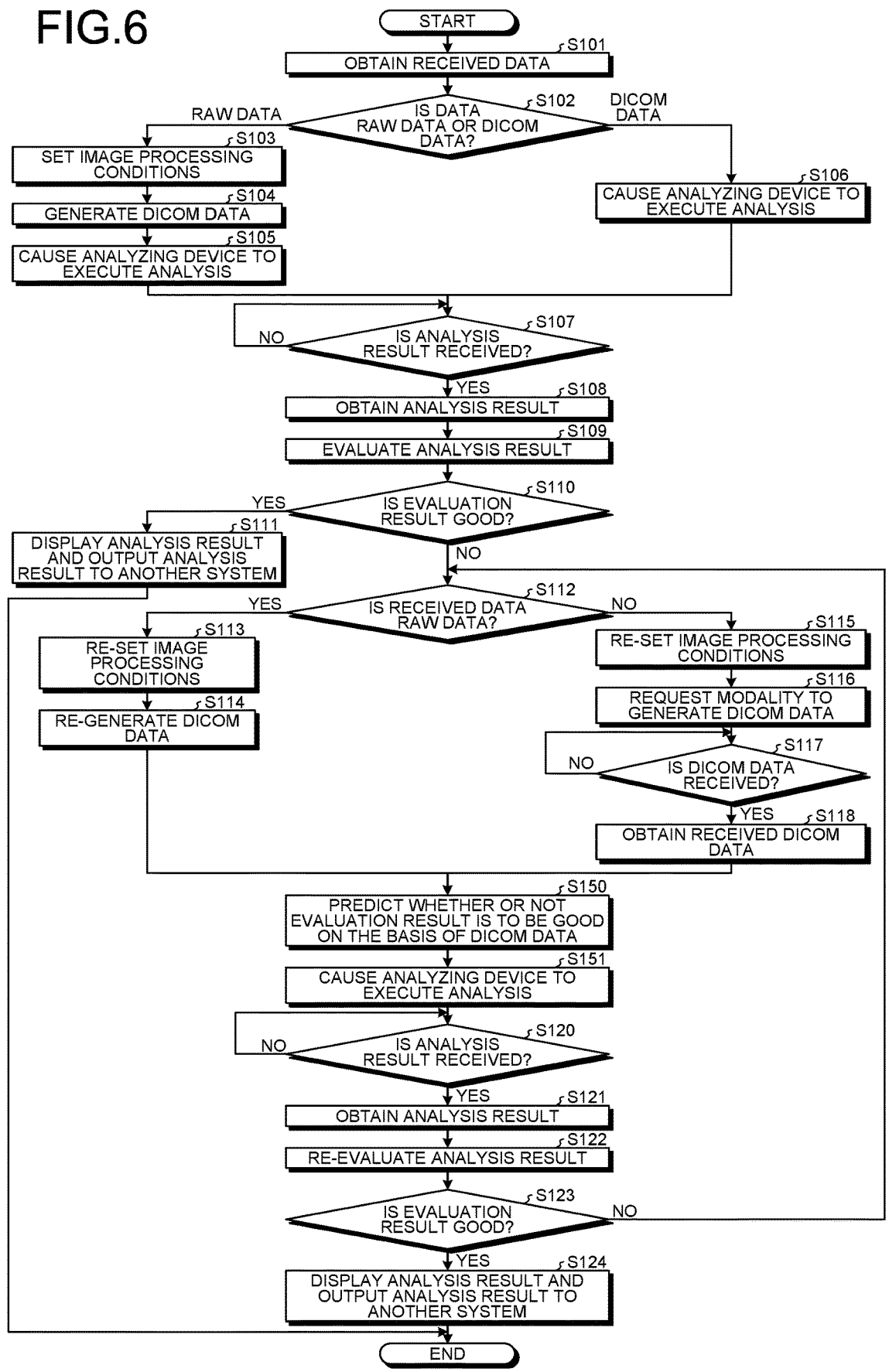
FIG. 6 is a flowchart illustrating a flow in an example of an analysis assisting process performed by an analysis assisting device according to a first modification example of the first embodiment.

FIG. 6 is a flowchart illustrating a flow in an example of an analysis assisting process performed by the analysis assisting device 150 according to the first modification example of the first embodiment. For example, the analysis assisting process is performed when raw data or DICOM data is received by the analysis assisting device 150, and the received raw data or DICOM data is stored in the storage circuit 152.

The analysis assisting process illustrated in FIG. 6 is different from the analysis assisting process illustrated in FIG. 2 for including processes at steps S150 and S151, in place of the process at step S119.

In the first modification example of the first embodiment, the analysis result obtained at step S108 or step S121 includes an error occurring when the noise reduction application failed to reduce noise, an error occurring when the body movement correction application failed to correct body movements, and a segmentation result obtained by the segmentation application or an error occurring when the segmentation application failed the segmentation process.

After that, at steps S109 and S110, the output function 155*c* determines that the analysis result is good when the analysis result does not include errors related to any of the applications, namely, the noise reduction application, the body movement correction application, and the segmentation application.

On the contrary, the output function 155*c* determines that the analysis result is not good when the analysis result includes one or more errors related to at least one of the applications among the noise reduction application, the body movement correction application, and the segmentation application. After that, the output function 155*c* stores information indicating one or more of the applications having the errors into the storage circuit 152. For example, the output function 155*c* stores information indicating that the errors occurred in the body movement correction application and the segmentation application, into the storage circuit 152.

Further, at steps S122 and S123, the output function 155*c* performs the same processes as those at steps S109 and S110.

After that, supposing that the process proceeds to step S123 on the basis of the DICOM data obtained at step S114 or step S118, the output function 155*c* predicts, at step S150, a judgment result as to whether or not the evaluation result is to be determined to be good at step S123. For example, at step S150, the output function 155*c* may predict a judgement result with respect to each of the applications. More specifically, the output function 155*c* may predict a judgment result with respect to each of the applications, namely, the noise reduction application, the body movement correction application, and the segmentation application.

More specifically, for example, the output function 155*c* judges whether or not the image data included in the DICOM data renders the entire region of the lungs. Further, when the image data renders the entire region of the lungs, the output function 155*c* predicts that the evaluation result of the segmentation application will be determined to be good. On the contrary, when the image data does not render the entire region of the lungs, the output function 155*c* predicts that the evaluation result of the segmentation application will not be determined to be good.

After that, at step S151, the fourth obtaining function 155*e* transmits the DICOM data obtained at step S114 or step S118 to the analyzing device 130 and causes the analyzing device 130 to execute the analysis application and to transmit an analysis result to the analysis assisting device 150.

In this situation, at step S151, the fourth obtaining function 155*e* transmits an instruction to the analyzing device 130, so as to cause the analyzing device 130 to execute one or more applications corresponding to the prediction result at step S150, from among the plurality of applications included in the analysis application. An example will be explained in which, for instance, at step S150, it is predicted that the evaluation results of the noise reduction application and the body movement correction application will be determined to be good, and it is predicted that the evaluation result of the segmentation application will not be determined to be good.

In this situation, even when the segmentation application is executed, there is a possibility that the evaluation result may not be determined to be good at step S123. For this reason, at step S151, the fourth obtaining function 155*e* transmits an instruction to the analyzing device 130 so as to cause the analyzing device 130 to execute the noise reduction application and the body movement correction application in accordance with the prediction result at step S150, from among the plurality of applications included in the analysis application. Accordingly, because the analyzing device 130 does not execute the segmentation application of which the evaluation result has a possibility of being determined to be not good, the analyzing device 130 is saved from executing the application that may have an error when being executed. Consequently, the analysis assisting system 100 and the analysis assisting device 150 according to the first modification example of the first embodiment are able to decrease processing loads.

Further, in the first modification example of the first embodiment, at step S121, the fourth obtaining function 155*e* obtains an analysis result obtained from the analysis corresponding to the prediction result.

Alternatively, at step S151, the fourth obtaining function 155*e* may transmit an instruction to the analyzing device 130 so as to cause the analyzing device 130 to execute one or more applications corresponding to the judgment result at step S110 or step S123, from among the plurality of applications included in the analysis application. An example will be explained in which, for instance, information indicating that errors occurred in the body movement correction application and the segmentation application is stored in the storage circuit 152 at step S110 or step S123.

In this situation, because the execution of the noise reduction application is completed, the analyzing device 130 does not need to execute the noise reduction application again. For this reason, at step S151, the fourth obtaining function 155e transmits an instruction to the analyzing device 130 so as to cause the analyzing device 130 to execute the body movement correction application and the segmentation application in accordance with the judgment result at step S110 or step S123, from among the plurality of applications included in the analysis application. Accordingly, because the analyzing device 130 does not execute the noise reduction application again of which the execution is completed, the analyzing device 130 is saved from executing the application that does not need to be executed. Consequently, the analysis assisting system 100 and the analysis assisting device 150 according to the first modification example of the first embodiment are able to decrease processing loads.

After that, in the first modification example of the first embodiment, the fourth obtaining function 155e obtains, at step S121, an analysis result obtained from the analysis corresponding to the judgment result.

The analysis assisting system 100 and the analysis assisting device 150 according to the first modification example of the first embodiment have thus been explained. The analysis assisting system 100 and the analysis assisting device 150 according to the first modification example of the first embodiment achieve the same advantageous effects as those achieved by the analysis assisting system 100 and the analysis assisting device 150 according to the first embodiment.

Second Modification Example of First Embodiment

As illustrated in FIG. 2, the processes at steps S112 through S123 are repeatedly performed until the evaluation result is determined to be good at step S123. Accordingly, when the analyzing device 130 executes the same analysis application, it may take a long period of time before the evaluation result is determined to be good at step S123, which means that the time period from the start to the end of the analysis assisting process may be long. To cope with this situation, when the evaluation result is determined to be not good at step S123 a predetermined number of times, the analysis assisting device 150 may instruct the analyzing device 130 to execute another analysis application of which the purpose is the same diagnosing process as that of the analysis application that has so far been used. Thus, this modification example will be explained as a second modification example of the first embodiment. In the description of the second modification example of the first embodiment, differences from the first embodiment will primarily be explained. The explanations of some of the elements that are the same as those in the first embodiment may be omitted.

For example, in the second modification example of the first embodiment, when the evaluation result is determined to be not good at step S123 the predetermined number of times, the fourth obtaining function 155e instructs the analyzing device 130 at step S119 or step S151 to execute another analysis application of which the purpose is the same diagnosing process as that of the analysis application that has so far been used.

Figure 7:
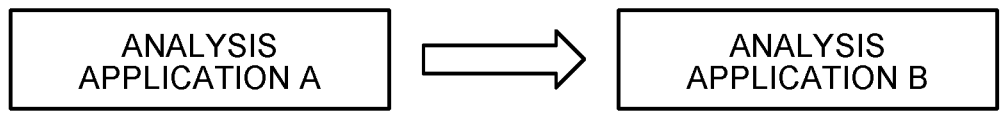
FIG. 7 is a drawing for explaining an example of a process performed by an analysis assisting device according to a second modification example of the first embodiment.

FIG. 7 is a drawing for explaining an example of a process performed by the analysis assisting device 150 according to the second modification example of the first embodiment. For example, when the evaluation result is determined to be not good at step S123 the predetermined number of times, the fourth obtaining function 155e instructs the analyzing device 130 at step S119 or step S151 to execute, as illustrated in FIG. 7, another analysis application (analysis application B) of which the purpose is the same diagnosing process as that of analysis application A that has so far been used. Accordingly, the analyzing device 130 executes the other analysis application (analysis application B) of which the purpose is the same diagnosing process as that of analysis application A that has so far been used. As a result, it is possible to shorten the time period from the time when the execution of the analysis assisting process is started to the time when the evaluation result is determined to be good at step S123. Consequently, the analysis assisting system 100 and the analysis assisting device 150 according to the second modification example of the first embodiment are able to shorten the processing time of the entire analysis assisting process. Thus, the analysis assisting system 100 and the analysis assisting device 150 according to the second modification example of the first embodiment are able to decrease processing loads in the analysis assisting process.

The analysis assisting system 100 and the analysis assisting device 150 according to the second modification example of the first embodiment have thus been explained. The analysis assisting system 100 and the analysis assisting device 150 according to the second modification example of the first embodiment achieve the same advantageous effects as those achieved by the analysis assisting system 100 and the analysis assisting device 150 according to the first embodiment.

Second Embodiment

In the first embodiment, the example was explained in which the analyzing device 130 is configured to perform the analysis on the image data included in the DICOM data, by executing the analysis application. However, it is also acceptable to configure the analysis assisting device 150 to perform an analysis on the image data included in the DICOM data, by executing an analysis application. Thus, this embodiment will be explained as a second embodiment. In the description of the second embodiment, differences from the first embodiment will primarily be explained. The explanations of some of the elements that are the same as those in the first embodiment may be omitted. For example, the same processes may be referred to by using the same reference characters as those in the first embodiment, and the explanations thereof may be omitted.

Figure 8:
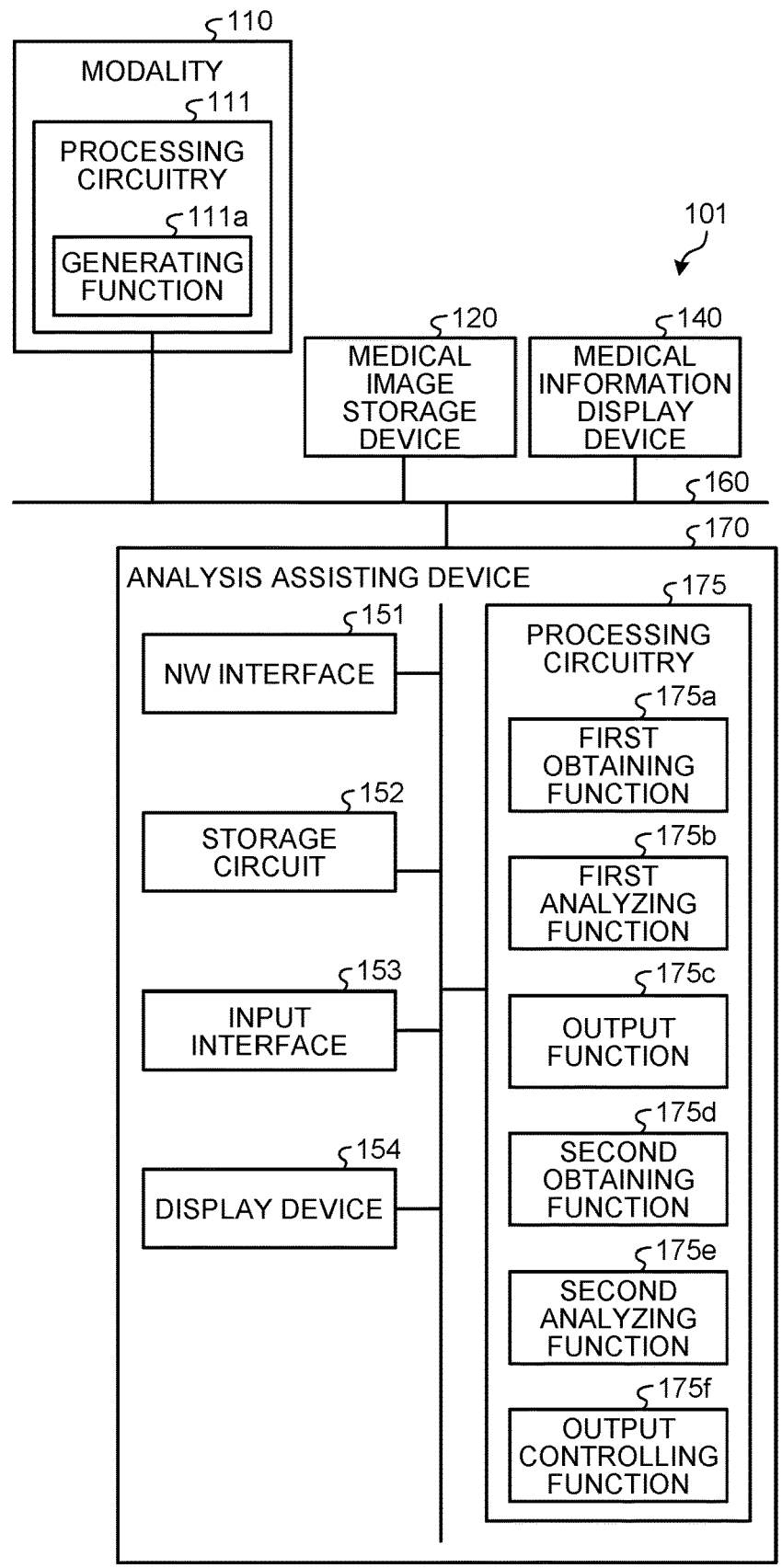
FIG. 8 is a diagram illustrating exemplary configurations of an analysis assisting system and an analysis assisting device according to a second embodiment.

FIG. 8 is a diagram illustrating exemplary configurations of an analysis assisting system 101 and an analysis assisting device 170 according to the second embodiment. The second embodiment is different from the first embodiment in that, in place of the analyzing device 130, the analysis assisting device 170 is configured to perform various types of processes by using an analysis result of analyzing the image data included in the DICOM data.

As illustrated in FIG. 8, the analysis assisting system 101 is different from the analysis assisting system 100 according to the first embodiment for including the analysis assisting device 170 in place of the analysis assisting device 150. Further, the analysis assisting system 101 is different from the analysis assisting system 100 according to the first embodiment for not including the analyzing device 130.

The analysis assisting device 170 is different from the analysis assisting device 150 according to the first embodiment for including processing circuitry 175 in place of the processing circuitry 155.

As illustrated in FIG. 8, the processing circuitry 175 includes a first obtaining function 175a, a first analyzing function 175b, an output function 175c, a second obtaining function 175d, a second analyzing function 175e, and an output controlling function 175f. The first obtaining function 175a is an example of a first obtaining unit. The first analyzing function 175b is an example of a first analyzing unit. The output function 175c is an example of an output unit. The second obtaining function 175d is an example of a second obtaining unit. The second analyzing function 175e is an example of a second analyzing unit. The output controlling function 175f is an example of an output controlling unit.

In this situation, for example, processing functions of the constituent elements of the processing circuitry 175 illustrated in FIG. 8, namely, the first obtaining function 175a, the first analyzing function 175b, the output function 175c, the second obtaining function 175d, the second analyzing function 175e, and the output controlling function 175f, are stored in the storage circuit 152 in the form of computer-executable programs. The processing circuitry 175 is configured to realize the functions corresponding to the programs, by reading the programs from the storage circuit 152 and executing the read programs. In other words, the processing circuitry 175 that has read the programs has the functions illustrated within the processing circuitry 175 in FIG. 8.

Figure 9:
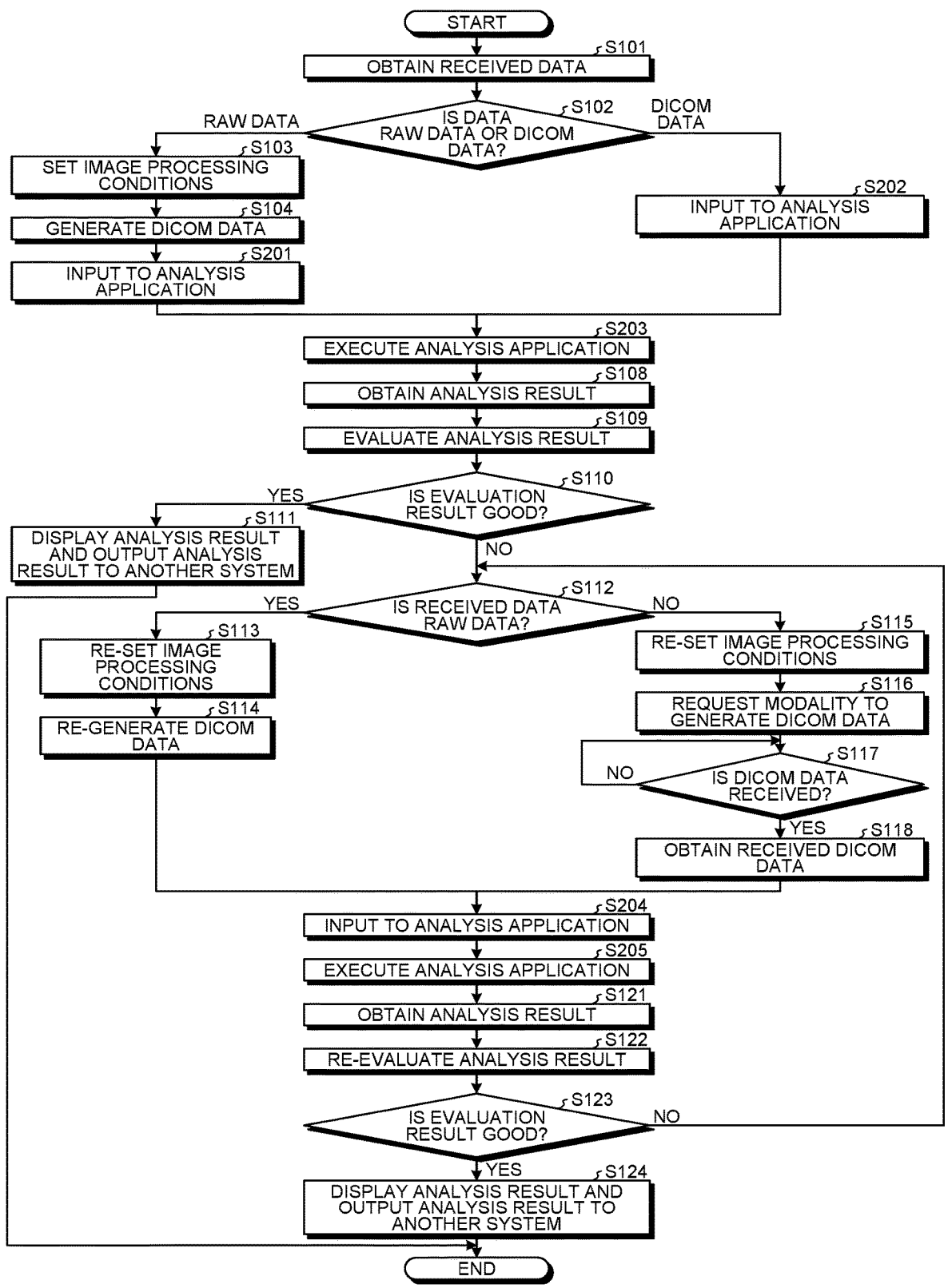
FIG. 9 is a flowchart illustrating a flow in an example of an analysis assisting process performed by the analysis assisting device according to the second embodiment.

FIG. 9 is a flowchart illustrating a flow in an example of an analysis assisting process performed by the analysis assisting device 170 according to the second embodiment. For example, the analysis assisting process is performed when raw data or DICOM data is received by the analysis assisting device 170, and the received raw data or DICOM data is stored in the storage circuit 152.

The analysis assisting process illustrated in FIG. 9 is different from the analysis assisting process illustrated in FIG. 2 for including the processes at steps S201 through S205, in place of the processes at steps S105 through S107, S119, and S120.

The first obtaining function 175a performs the processes at steps S101 through S104. Further, the first analyzing function 175b performs the processes at steps S201 through S203 and S108. Also, the output function 175c performs the processes at steps S109, S110, S112, S113, S115, S122, and S123. In addition, the second obtaining function 175d performs the processes at steps S114 and S116 through S118. Further, the second analyzing function 175e performs the processes at steps S204, S205, and S121. Furthermore, the output controlling function 175f performs the processes at steps S111 and S124. Among all the steps illustrated in FIG. 9, at some of the steps having the same reference numbers as those assigned to the steps illustrated in FIG. 2, the same processes as those at the steps identified with the same reference numbers in FIG. 2 are performed.

The first analyzing function 175b inputs the DICOM data obtained at step S104 to the analysis application (step S201). Further, the first analyzing function 175b inputs the DICOM data obtained at step S101 to the analysis application (step S202). After that, the first analyzing function 175b executes the analysis application (step S203). Further, the first analyzing function 175b obtains an analysis result output by the analysis application executed at step S203 (step S108).

As explained above, the first analyzing function 175b obtains, in the processes at steps S201 through S203 and S108, the analysis result (a first analysis result) from the analysis performed on the DICOM data obtained at step S101 or S104.

The second analyzing function 175e inputs the DICOM data obtained at step S114 or S118 to the analysis application (step S204). After that, the second analyzing function 175e executes the analysis application (step S205). Further, the second analyzing function 175e obtains an analysis result output by the analysis application executed at step S205 (step S121).

As explained above, the second analyzing function 175e obtains, in the processes at steps S204, S205, and S121, the analysis result (a second analysis result) from the analysis performed on the DICOM data obtained at step S114 or S118.

The analysis assisting system 101 and the analysis assisting device 170 according to the second embodiment have thus been explained. The analysis assisting system 101 and the analysis assisting device 170 according to the second embodiment achieve the same advantageous effects as those achieved by the analysis assisting system 100 and the analysis assisting device 150 according to the first embodiment.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). When the processor is a CPU, for example, the processor is configured to realize the functions by reading and executing the programs saved in a memory. In contrast, when the processor is an ASIC, for example, instead of having the programs saved in the memory, the functions are directly incorporated in the circuitry of the processor as a logic circuit. Further, the processors of the present embodiments do not each necessarily have to be structured as a single circuit. It is also acceptable to structure one processor by combining together a plurality of independent circuits so as to realize the functions thereof.

The programs executed by the one or more processors are provided as being incorporated in advance in a Read-Only Memory (ROM), a storage circuit, or the like. The programs may be provided as being recorded on a non-transitory computer-readable storage medium such as a Compact Disk Read-Only Memory (CD-ROM), a Flexible Disk (FD), a Compact Disk Recordable (CD-R), or a Digital Versatile Disk (DVD), in a file that is in an installable or executable format for the devices. Further, the programs may be stored in a computer connected to a network such as the Internet so as to be provided or distributed as being downloaded via the network. For example, the programs are structured with modules including the processing functions described above. In actual hardware, as a result of a CPU reading and executing the programs from the storage medium such as the ROM, the modules are loaded into a main storage device so as to be generated in the main storage device.

According to at least one aspect of the embodiments and the modification examples described above, it is possible to enhance the precision level of the analysis result.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analysis assisting device, comprising:
processing circuitry configured to:
   obtain first analysis image data based on image data taken of a patient and additional information of the image data;
   obtain a first analysis result of analyzing the first analysis image data;
   output, when the first analysis result does not satisfy a predetermined condition, an image processing condition optimal for the analysis;
   obtain second analysis image data by generating the second analysis image data by performing an image processing process based on the image processing condition, or obtain the second analysis image data generated as a result of an external device performing an image processing process based on the image processing condition;
   predict, based on the second analysis image data, whether or not a second analysis result of analyzing the second analysis image data will satisfy the predetermined condition; and
   obtain an analysis result obtained by performing an analysis corresponding to the prediction result on the second analysis image data.

2. The analysis assisting device according to claim 1, wherein
   when the first analysis result of analyzing the first analysis image data does not satisfy the predetermined condition, the processing circuitry is further configured to repeatedly change the image processing condition until a third analysis result of analyzing newly-obtained third analysis image data satisfies the predetermined condition,
   every time the image processing condition is changed, the processing circuitry is further configured to obtain the third analysis image data by generating the third analysis image data based on the changed image processing condition, or obtain the third analysis image data generated as a result of the external device performing the image processing process based on the changed image processing condition, and
   the processing circuitry is further configured to obtain the third analysis result from the third analysis image data satisfying the predetermined condition, as the second analysis result of analyzing the second analysis image data.

3. The analysis assisting device according to claim 2, wherein
   based on the third analysis image data, the processing circuitry is further configured to predict whether or not the third analysis result of analyzing the third analysis image data will satisfy the predetermined condition, and
   the processing circuitry is further configured to obtain the third analysis result from the third analysis image data being obtained from the analysis corresponding to the prediction result and satisfying the predetermined condition, as the second analysis result of analyzing the second analysis image data.

4. The analysis assisting device according to claim 2, wherein
   the processing circuitry is further configured to judge whether or not the third analysis result of analyzing the third analysis image data satisfies the predetermined condition, and
   the processing circuitry is further configured to obtain the third analysis result from the third analysis image data being obtained from the analysis corresponding to a result of the judgment and satisfying the predetermined condition, as the second analysis result of analyzing the second analysis image data.

5. The analysis assisting device according to claim 2, further comprising a display configured to output a message indicating a process for performing re-processing is underway, while any of the following is performed: a process of changing the image processing condition; a process of obtaining the third analysis image data;
   and a process of obtaining the second analysis result of analyzing the second analysis image data.

6. The analysis assisting device according to claim 2, further comprising a display configured to output the changed image processing condition while a process of changing the image processing condition is performed.

7. The analysis assisting device according to claim 2, wherein
   every time the third analysis image data is obtained, the processing circuitry is further configured to judge whether or not the third analysis result of analyzing the third analysis image data satisfies the predetermined condition, and
   the processing circuitry is further configured to obtain the third analysis result from the third analysis image data obtained by using an analysis application corresponding to a result of the judgment.

8. The analysis assisting device according to claim 1, further comprising a display configured to, when the first analysis result of analyzing the first analysis image data does not satisfy the predetermined condition, display a message indicating that the analysis failed under the image processing condition used at the time of generating the first analysis image data.

9. An analysis assisting device, comprising:
processing circuitry configured to:
   obtain first analysis image data based on an image taken of a patient and additional information of the image;
   analyze the first analysis image data to obtain a first analysis result:
   output, when the first analysis result does not satisfy a predetermined condition, an image processing condition optimal for the analysis;
   obtain second analysis image data by generating the second analysis image data by performing an image processing process based on the image processing condition, or obtain the second analysis image data generated as a result of an external device performing an image processing process based on the image processing condition;
   predict, based on the second analysis image data, whether or not a second analysis result of analyzing the second analysis image data will satisfy the predetermined condition; and
   perform an analysis corresponding to the prediction result on the second analysis image data.

10. An analysis assisting system comprising a medical image generating device and an analysis assisting device, wherein
the medical image generating device includes first processing circuitry configured to generate first analysis image data based on an image taken of a patient and additional information of the image, and
the analysis assisting device includes second processing circuitry configured to:
obtain the first analysis image data;
obtain a first analysis result of analyzing the first analysis image data;
output, when the first analysis result does not satisfy a predetermined condition, an image processing condition optimal for the analysis;
obtain second analysis image data by generating the second analysis image data by performing an image processing process based on the image processing condition, or obtain the second analysis image data generated as a result of an external device performing an image processing process based on the image processing condition;
predict, based on the second analysis image data, whether or not a second analysis result of analyzing the second analysis image data will satisfy the predetermined condition; and
obtain an analysis result obtained by performing an analysis corresponding to the prediction result on the second analysis image data.

11. An analysis assisting system comprising a medical image generating device and an analysis assisting device, wherein
the medical image generating device includes first processing circuitry configured to generate first analysis image data obtained based on an image taken of a patient and additional information of the image, and
the analysis assisting device includes second processing circuitry configured to:
obtain the first analysis image data;
analyze the first analysis image data;
output, when a first analysis result of the analysis does not satisfy a predetermined condition, an image processing condition optimal for the analysis;
obtain second analysis image data by generating the second analysis image data by performing an image processing process based on the image processing condition, or obtain the second analysis image data generated as a result of an external device performing an image processing process based on the image processing condition;
predict, based on the second analysis image data, whether or not a second analysis result of analyzing the second analysis image data will satisfy the predetermined condition; and
perform an analysis corresponding to the prediction result on the second analysis image data.

12. A non-transitory computer-readable recording medium having recorded thereon a program that causes a computer to perform:
obtaining first analysis image data based on an image taken of a patient and additional information of the image;
obtaining a first analysis result of analyzing the first analysis image data;
outputting, when the first analysis result does not satisfy a predetermined condition, an image processing condition optimal for the analysis;
obtaining second analysis image data by generating the second analysis image data by performing an image processing process based on the image processing condition, or obtaining the second analysis image data generated as a result of an external device performing an image processing process based on the image processing condition;
predicting, based on the second analysis image data, whether or not a second analysis result of analyzing the second analysis image data will satisfy the predetermined condition; and
obtaining an analysis result obtained by performing an analysis corresponding to the prediction result on the second analysis image data.

13. A non-transitory computer-readable recording medium having recorded thereon a program that causes a computer to perform:
obtaining first analysis image data based on an image taken of a patient and additional information of the image;
analyzing the first analysis image data to obtain a first analysis result;
outputting, when the first analysis result does not satisfy a predetermined condition, an image processing condition optimal for the analysis;
obtaining second analysis image data by generating the second analysis image data by performing an image processing process based on the image processing condition, or obtaining the second analysis image data generated as a result of an external device performing an image processing process based on the image processing condition;
predicting, based on the second analysis image data, whether or not a second analysis result of analyzing the second analysis image data will satisfy the predetermined condition; and
performing an analysis corresponding to the prediction result on the second analysis image data.

* * * * *